(12) United States Patent
Danilkovich et al.

(10) Patent No.: US 8,637,004 B2
(45) Date of Patent: Jan. 28, 2014

(54) PURIFIED MESENCHYMAL STEM CELL COMPOSITIONS AND METHODS OF PURIFYING MESENCHYMAL STEM CELL COMPOSITIONS

(75) Inventors: Alla Danilkovich, Columbia, MD (US); Robert E. Newman, Jr., Sykesville, MD (US); Samson Tom, Baltimore, MD (US); Christopher Ton, Baltimore, MD (US); Zhanling Wang, West Chester, PA (US); Randell G. Young, Ellicott City, MD (US)

(73) Assignee: Mesoblast International Sarl (CH)

( * ) Notice: Subject to any disclaimer, the term of this patent is extended or adjusted under 35 U.S.C. 154(b) by 803 days.

(21) Appl. No.: 12/541,282

(22) Filed: Aug. 14, 2009

(65) Prior Publication Data

US 2010/0068191 A1 Mar. 18, 2010

Related U.S. Application Data

(60) Provisional application No. 61/088,898, filed on Aug. 14, 2008.

(51) Int. Cl.
*C12N 5/00* (2006.01)

(52) U.S. Cl.
USPC .................................. 424/93.7; 435/325

(58) Field of Classification Search
None
See application file for complete search history.

(56) References Cited

U.S. PATENT DOCUMENTS

| | | | |
|---|---|---|---|
| 5,034,135 A | 7/1991 | Fischel | |
| 5,053,121 A | 10/1991 | Schoendorfer et al. | |
| 5,197,985 A | 3/1993 | Caplan et al. | |
| 5,226,914 A | 7/1993 | Caplan et al. | |
| 5,234,608 A | 8/1993 | Duff | |
| 5,486,359 A * | 1/1996 | Caplan et al. | 424/93.7 |
| 5,536,475 A | 7/1996 | Moubayed et al. | |
| 5,707,996 A * | 1/1998 | Parrinello | 514/256 |
| 5,827,740 A * | 10/1998 | Pittenger | 435/372 |
| 5,837,539 A | 11/1998 | Caplan et al. | |
| 5,855,619 A * | 1/1999 | Caplan et al. | 623/23.72 |
| 6,087,113 A | 7/2000 | Caplan et al. | |
| 6,251,295 B1 | 6/2001 | Johnson | |
| 6,387,369 B1 * | 5/2002 | Pittenger et al. | 424/93.7 |
| 7,390,484 B2 | 6/2008 | Fraser et al. | |
| 2002/0115219 A1 * | 8/2002 | Kobayashi et al. | 435/470 |
| 2003/0054331 A1 | 3/2003 | Fraser et al. | |
| 2003/0161816 A1 | 8/2003 | Fraser et al. | |
| 2004/0096431 A1 | 5/2004 | Fraser et al. | |
| 2004/0097867 A1 | 5/2004 | Fraser et al. | |
| 2004/0106196 A1 | 6/2004 | Fraser et al. | |
| 2005/0008626 A1 | 1/2005 | Fraser et al. | |
| 2005/0048033 A1 | 3/2005 | Fraser et al. | |
| 2005/0048034 A1 | 3/2005 | Fraser et al. | |
| 2005/0048035 A1 | 3/2005 | Fraser et al. | |
| 2005/0048036 A1 | 3/2005 | Hedrick et al. | |
| 2005/0074436 A1 | 4/2005 | Fraser et al. | |
| 2005/0084961 A1 | 4/2005 | Hedrick et al. | |
| 2005/0095228 A1 | 5/2005 | Fraser et al. | |
| 2005/0260174 A1 | 11/2005 | Fraser et al. | |
| 2005/0260175 A1 | 11/2005 | Hedrick et al. | |
| 2006/0083720 A1 | 4/2006 | Fraser et al. | |
| 2007/0036768 A1 | 2/2007 | Fraser et al. | |
| 2008/0175825 A1 | 7/2008 | Hampson et al. | |

FOREIGN PATENT DOCUMENTS

| | | |
|---|---|---|
| WO | 03/024215 | 3/2003 |
| WO | 03/053346 | 7/2003 |
| WO | 2005/012480 | 2/2005 |
| WO | 2007/035843 | 3/2007 |
| WO | 2007/089798 | 8/2007 |
| WO | 2008/054825 | 5/2008 |
| WO | 2008/073331 | 6/2008 |

OTHER PUBLICATIONS

Pittenger MF et al. 1999. Multilineage Potential of Adult Human Mesenchymal Stem Cells. Science 284: 143-147, plus online supplementary material.*
Zhang L et al. 2010. Isolation and Enrichment of Rat Mesenchymal Stem Cells (MSCs) and Separation of Single-colony Derived MSCs. J. Vis. Exp. (37), e1852, DOI : 10.3791/1852. 4 pages.*
International Search Report and Written Opinion for International Patent Application Serial No. PCT/US2009/53891, dated Oct. 14, 2009.
Saraji, "Dynamic headspace liquid-phase microextraction of alcohols." Journal of Chromatography A, Jan. 7, 2005, vol. 1062, pp. 15-21.
Syringe Needle Conversion Chart. Designer-Drugs.com. Retrieved from the Internet Sep. 28, 2009, http://web.archive.org/web/20080411091808/http://designer-drugs.com/pte/12.162.180.114/dcd/chemistry/equipment/needleguage.html.
International Preliminary Examination Report in PCT/US2009/053891, dated Feb. 24, 2011.
Bindslev-Jensen et al., Allergy, 57:741-746 (2002).
Calmels et al., Bone Marrow Transplant., 31(9):823-828 (2003).
Colten et al., N. Engl. J. Med., 292:1050-1053 (1975).
de Benito et al., Allergol. Immunopathol. (Madr.), 29:272-275 (2001).

(Continued)

*Primary Examiner* — L B Driscoll
(74) *Attorney, Agent, or Firm* — McAndrews, Held & Malloy, Ltd.

(57) ABSTRACT

One or more purified mesenchymal stem cell pharmaceutical compositions and methods of manufacture utilizing centrifugal filtration are disclosed. Threshold limits for intravenous administration of mesenchymal stem cell pharmaceutical compositions comprising residual animal products are also disclosed.

15 Claims, 4 Drawing Sheets
(3 of 4 Drawing Sheet(s) Filed in Color)

(56) References Cited

OTHER PUBLICATIONS

Hilton et al., Food Chem. Toxicol., 35:1209-1218 (1997).
Moneret-Vautrin et al., Allergy, 46:228-234 (1991).
Moneret-Vautrin et al., Curr. Opin. Allergy Clin. Immunol., 4:215-219 (2004).
Orta et al., Ann. Alergy Asthma Immunol., 90:446-451 (2003).
Perotti et al., Transfusion, 44(6):900-906 (2004).
Shepard et al., Infect. Immun., 38:673-680 (1982).
Spees et al., Mol. Ther., 9:747-756 (2004).
Taylor et al., Clin. Exp. Allergy, 34:689-695 (2004).
Wensing et al., J. Allergy Clin. Immunol., 110:915-220 (2002).

* cited by examiner

Figure 1: Exemplary apparatus for washing MSCs.

Figure 2: Un-purified MSC composition viewed with 10x magnification.

Figure 3: MSC composition purified by centrifugation viewed with 10x magnification.

Figure 4: MSC composition purified by centrifugal filtration viewed with 10x magnification.

PURIFIED MESENCHYMAL STEM CELL COMPOSITIONS AND METHODS OF PURIFYING MESENCHYMAL STEM CELL COMPOSITIONS

RELATED APPLICATIONS

This application claims the priority of U.S. Provisional Patent Application Ser. No. 61/088,898, filed on Aug. 14, 2008, the contents of which are incorporated herein by reference.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Mesenchymal stem cells ("MSC" or "MSCs") can be found in bone marrow, blood, dermis, periosteum and other tissues of the body, and are capable of differentiating into a variety of cell types, including adipose, areolar, osseous, cartilaginous, elastic, marrow stroma, muscle, fibrous connective tissue, and cardiac tissue, depending upon various in vivo or in vitro factors and influences. Such cells are disclosed, for example, in U.S. Pat. Nos. 5,197,985; 5,226,914; 5,486,359; 5,837,539, and 6,087,113, each of which are independently incorporated by reference in their entirety.

MSCs have been shown to engraft and selectively differentiate, based on the tissue environment, to lineages such as muscle, bone, cartilage, marrow stroma, tendon and fat. Due to their cellular origin and phenotype, these cells do not provoke an adverse immune response, allowing for the development of products derived from unrelated human donors.

In general, MSCs are isolated from the tissue from which they are obtained, purified, and then expanded in an appropriate culture medium. The culture medium contains a variety of components that support the expansion of the MSCs, such as serum, which comprises serum proteins (e.g., serum albumin, such as bovine serum albumin); growth factors; and cytokines. After isolation, purification, and culture expansion, the MSCs are subjected to a series of washes and, optionally, centrifugation. The MSCs then may be frozen and stored in an appropriate cryopreservation medium, for example a cryopreservation medium comprising dimethyl sulfoxide ("DMSO"). Subsequently, the MSCs are thawed just prior to administration to a patient.

The manufacturing process for the expansion of MSCs involves cell culturing in the presence of non-autologous serum and cell harvesting by non-autologous trypsin; in some processes, the non-autologous serum is fetal bovine serum ("FBS") and the non-autologous trypsin is porcine trypsin. The ex vivo expansion of human MSCs ("hMSCs") using animal reagents leads to the presence of residual macromolecules of non-human origin (for example, macro-molecules of porcine and bovine origin) in the ultimate product. After expanding hMSCs in media comprising non-human products, an increased amount of xenogeneic substances can be observed relative to hMSCs expanded in media comprising human products.

Bovine serum albumin ("BSA") is a significant component of FBS. Both BSA and porcine trypsin are known allergens. As such, they can trigger adverse reactions in patients susceptible to bovine and porcine macro-molecules, and can cause non-allergic patient sensitization leading to allergic reactions upon multiple exposures (See, e.g., Cotten HR et al., N Engl J Med, 1975, 292:1050; Moneret-Vautrin A. et al., Allergy, 1991, 46:228; Orta M et al., Ann Allergy Asthma Immunol 2003, 90:446; de Benito V. et al., Allergologia et Immunopathologia, 2001, 29:272). Increased amounts of FBS present in culturally expanded MSCs also may induce undesired side effects in patients, such as undesirable immune responses, pulmonary embolism, vasoconstriction, cardiac shock, or death. The presence of residual BSA or porcine trypsin may increase immunogenicity and accelerate clearance or elimination of MSCs from the recipient. Increased amounts of FBS present in pharmaceutical compositions comprising culturally expanded MSCs can increase the risk of transmitting viruses, prion diseases, and xenogeneic proteins to patients receiving such MSC-based therapies. Increased amounts of FBS, particularly BSA, present in pharmaceutical compositions comprising culture-expanded hMSCs may initiate immune responses against these xenogeneic substances. For example, if the MSC preparation administered to a patient contains BSA or other xenogeneic proteins, such xenogeneic proteins may trigger an undesirable immune response. Xenogeneic proteins may elicit cell-mediated or humoral immune responses (e.g., the generation of anti-bovine serum protein antibodies), which may result in less efficient engraftment of the MSCs, particularly if such xenogeneic proteins become associated with MSC cell-surface membranes. As such, a new approach is needed to reduce the amount of xenogeneic substances, including FBS, and particularly BSA, present in pharmaceutical compositions comprising culturally expanded MSCs. A new approach is needed to reduce the amount of xenogeneic substances, including sugars, proteins and other macromolecules present in culture expanded MSCs, which could increase the safety profile of the resultant MSC composition.

Media comprising alternative sera such as autologous human serum have been proposed, however, the use of autologous serum is not possible when the quantities of cells required in the ultimate MSC product exceed that which can be grown in a fixed amount of autologous serum. Additionally, the use of autologous human serum presupposes that the patient will have sufficient time and be in sufficient health to donate serum in advance of the initiation of MSC therapy. The current conventional MSC culturing process typically requires 2 to 10 weeks to isolate, expand, harvest and purify a suitable number of cells to constitute a pharmaceutical treatment. In some cases, a pharmaceutical treatment consists of 1 dose. In other cases, a pharmaceutical treatment consists of 2 or more doses. Unfortunately, in some cases, MSC therapy is needed less than about 2 weeks from diagnosis or presentation of clinical symptoms, or in less than about 1 week from diagnosis or presentation of clinical symptoms, or in less than about 48 hours of diagnosis or presentation of clinical symptoms. When MSC therapy is needed within a short time period from diagnosis or presentation of clinical symptoms, hMSCs that have already been manufactured, purified and cryopreserved exhibit the significant benefit of being available upon diagnosis or presentation of an acute illness.

Moreover, human serum, including autologous human serum, exhibits a statistically significant increase in the risk of transmitting a disease, for example, a viral disease, to the recipient of the MSC pharmaceutical composition.

Spees et al., mention combinations of media comprising serial passages in fetal calf serum ("FCS") and autologous human serum. (Spees et al., *Mol Therapy*, 2004, 9: 747). Final compositions produced by serial combinations of media yielded greater than a 15-fold range in residual FCS per sample according to SDS-Page electrophoresis of labeled FCS after 50 wash cycles. Protocols requiring autologous human serum and extensive washing that do not provide more reproducible final compositions are academically interesting, but do not provide the quality or consistency required to manufacture a pharmaceutical composition suitable for administration to a human.

Risk doses and thresholds for clinical reactivity among allergic patients have been established for a number of antigens. (Moneret-Vautrin A. & Kanny G., *Curr Opin Allergy Clin Immunol*, 2004, 4:215; Bindslev-Jensen C et al., *Allergy*, 2002, 57:741). Though these thresholds are established for oral administration of antigens, thresholds for intravenous ("IV") exposure to allergens are unknown. (Wensing M. et al., *J Allergy Clin Immunol*, 2002, 110:915; Taylor SL et al., *Clin Exp Allergy*, 2004, 34:689). Therapeutic decisions regarding IV administration of compositions comprising MSCs are complicated by the absence of threshold data and reports in the literature showing that cellular and animal-derived products may cause serious adverse reactions (for example, anaphylaxis and serum sickness-like disease). (Moneret-Vautrin A et al., *Allergy*, 1991, 46:228; Orta M et al., *Ann Allergy Asthma Immunol* 2003, 90:446; de Benito V. et al., *Allergologia et lmmunopathologia*, 2001, 29:272).

As an example, risk doses and thresholds for clinical reactivity among allergic patients are established for a number of antigens, most of which relate to food allergen categories (Moneret-Vautrin A. & Kanny G., *Curr Opin Allergy Clin Immunol*, 2004, 4:21). Because these thresholds were established for oral administration of antigens, they are expected to be different from thresholds for IV administration. Again, thresholds for IV exposure to allergens remain unknown. (Taylor SL et al. *Clin Exp Allergy*, 2004, 34:689). The absence of threshold data and reports in the literature showing that cellular and animal-derived products may cause serious adverse reactions (for example, anaphylaxis and serum sickness like disease) exclude use of therapeutics manufactured in the presence of bovine or porcine products. (Orta M. et al., *Ann Allergy Asthma Immunol* 2003, 90:446).

Perotti et al mention centrifugal filtration as a technique useful for removing the cryopreservative DMSO from umbilical cord blood. (Perotti CG et al., *Transfusion*, 2004, 44(6):900-906). Calmels et al. mention centrifugal filtration as a technique useful for removing DMSO from hematopoietic stem cell grafts. (Calmels B et al., *Bone Marrow Transplant.*, 2003, 31(9):823-828). Hampson et al. mention methods to wash cultured bone marrow mononuclear cells. (US 2008/0175825). Post-wash residual BSA levels from the cell culture supernatant were reported to be about less than 3 µg/ml. Using a Cytomate instrument to wash bone marrow mononuclear cells, Hampson et al. obtained about 70% cell viability post-wash. Hampson et al. indicated that this significant drop in cell viability may have been due to cellular damage caused by mechanical forces applied during the process.

Protocols requiring extensive washing of cells do not provide the quality or consistency required to manufacture a pharmaceutical composition suitable for administration to a human. Furthermore, the effects of extensive washing protocols on the viability of cells and the efficacy a pharmaceutical composition comprising such cells is unknown.

Additionally, many published purification protocols comprise at least one step involving transfer of the MSC-containing intermediate product where the product is exposed to the external environment (i.e. not a closed system). As closed systems carefully control the quantity and quality of materials entering and leaving the system, as well as the manner by which these materials enter or leave, the development of a closed manufacturing system for the preparation of MSC pharmaceutical compositions would represent a significant accomplishment in the art.

With these challenges in mind, it is necessary to: 1) establish a threshold dose for residual components in the product that will minimize risk of allergic reactions in patients; 2) provide a method for purifying an hMSC composition to reduce the amount of residual components, including allergens, below the threshold level, while minimizing cellular damage and maintaining cell viability; and, 3) provide an hMSC composition comprising less than the threshold amount of residual components, including allergens, limited cellular damage, and a high proportion of viable cells.

In summary, the state of the art related to methods of preparing pharmaceutical MSC compositions comprises one significant long felt need: reducing the immunogenicity of MSC compositions cultured in non-human serum. Further, the present technology described and claimed herein surprisingly identified a challenge that had not been previously recognized in the conventional art as a significant shortcoming: reducing the extent of MSC aggregation.

BRIEF DESCRIPTION OF THE INVENTION

Some embodiments of the present technology disclose pharmaceutical compositions comprising MSCs that have reduced immunogenicity relative to MSC compositions purified by centrifugation.

Some embodiments of the present technology disclose pharmaceutical compositions comprising MSCs that exhibit a reduced $D_{90}$ of any MSC aggregates present in the pharmaceutical composition.

Some embodiments of the present technology disclose pharmaceutical compositions comprising MSCs that exhibit decreased adhesion of individual MSCs to each other.

Some embodiments of the present technology disclose pharmaceutical compositions comprising MSCs wherein the MSCs are purified by centrifugal filtration after culture expansion.

Some embodiments of the present technology disclose pharmaceutical compositions comprising MSCs purified by centrifugal filtration that simultaneously (i) reduces the immunogenicity of MSC compositions; and, (ii) reduces the average size of MSC aggregates by decreasing the adhesive properties of individual MSCs.

Some embodiments of the present technology disclose pharmaceutical compositions comprising purified MSCs with a reduced immunogenicity and a reduced tendency to aggregate. Other embodiments of the present technology disclose pharmaceutical compositions comprising MSCs purified by centrifugal filtration. The process simultaneously (i) reduces the immunogenicity of MSC compositions; and, (ii) reduces the average size of MSC aggregates.

Some embodiments of the present technology disclose pharmaceutical compositions comprising MSCs and DMSO.

Further, some embodiments of the present technology disclose pharmaceutical compositions comprising MSCs that have been purified to reduce the quantity of xenogeneic substances such as proteins present after expansion in culture medium comprising, for example, BSA. Such pharmaceutical compositions exhibit superior safety profiles through, for example, the reduction of immunogenicity of such compositions.

Other embodiments of the present technology disclose pharmaceutical compositions comprising MSCs that have been purified to reduce the quantity of substances including cell surface membrane molecules, extracellular nucleic acids (DNA/RNA), and other cellular debris. Such pharmaceutical compositions may exhibit superior safety profiles by decreasing the average size of MSC aggregates by, for example, reducing the adhesive properties of individual MSCs. Such reduction in adhesive properties may effectuate a decrease in the average size of MSC aggregates.

Moreover, some embodiments of the present technology relate to compositions comprising culturally expanded hMSCs having reduced amounts of residual FBS components, particularly BSA, relative to a comparable lot of un-purified, culturally expanded MSCs. In some of these embodiments, the quantity of BSA in the compositions comprising the culturally expanded MSCs after purification is about 10 to 1,000-fold less than the quantity present in a comparable lot of un-purified, culturally expanded MSCs.

Still further embodiments of the present technology relate to purified human mesenchymal stem cells, and to methods of purifying human mesenchymal stem cells. More particularly, certain embodiments relate to pharmaceutical compositions including hMSCs in which the amount of extracellular, cell surface and transmembrane molecules in such compositions is reduced by 1 log (as used herein, the term "log" refers to base 10 log) relative to a comparable lot of un-purified, culturally expanded hMSCs. Other embodiments relate to one or more pharmaceutical compositions comprising less than about 10 µg/mL residual BSA. Some embodiments of this technology relate to a pharmaceutical composition comprising MSCs exhibiting a $D_{90}$ between about 18 µm and about 25 µm.

In additional embodiments, the present technology relates to methods of manufacturing pharmaceutical compositions comprising culturally expanded hMSCs in which the amount of extracellular, cell surface and transmembrane molecules in such compositions is reduced by 1 log relative to a comparable lot of un-purified, culturally expanded hMSCs. Other embodiments relate to a method of manufacturing pharmaceutical compositions comprising culturally expanded hMSCs comprising less than about 10 µg/mL residual BSA. Further embodiments relate to a method of manufacturing pharmaceutical compositions comprising culturally expanded hMSCs comprising hMSCs exhibiting a $D_{90}$ between about 18 µm and about 25 µm. Some embodiments of the present technology relate to pharmaceutical MSC compositions, wherein the composition comprises less than about 10 µg/mL residual BSA and the MSCs exhibit a $D_{90}$ between about 18 µm and about 25 µm.

Further embodiments of the present technology relate to compositions comprising culturally expanded hMSCs having reduced amounts of xenogeneic substances, including sugars, proteins and other macromolecules relative to a comparable lot of un-purified, culturally expanded MSCs. In some embodiments, the quantity of xenogeneic substances in the compositions comprising the culturally expanded MSCs after purification is about 1 log less than the quantity present in a comparable lot of un-purified, culturally expanded MSCs.

In still additional embodiments, the present technology relates to the establishment of a threshold quantity of residual components in an hMSC product that will minimize risk of allergic reactions in patients, particularly in patients receiving such a product by an IV route.

Moreover, in some embodiments, the present technology relates to methods of purifying hMSCs in which an hMSC preparation is purified by contacting the preparation with a wash solution, agitating the preparation, and recovering purified hMSCs.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
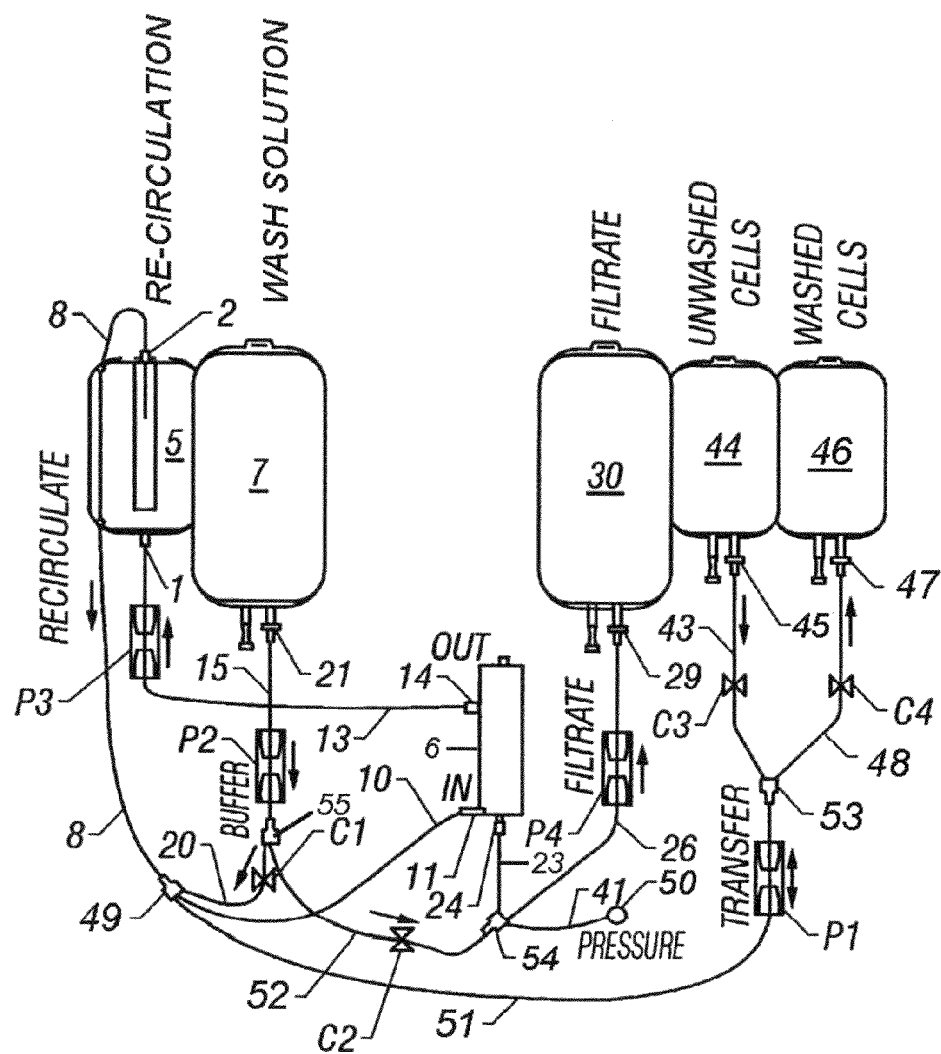
FIG. 1 is an exemplary apparatus that may be used to wash and purify mesenchymal stem cells according to an embodiment of the present technology.

Some embodiments of the present technology solve the previously recognized challenge of providing a pharmaceutical MSC composition having reduced quantities of xenogeneic substances. Some embodiments of the present technology also identify and solve the heretofore unrecognized challenge of providing a pharmaceutical MSC composition having reduced tendency to aggregate. Individually and collectively, these two solutions provide pharmaceutical MSC compositions, particularly pharmaceutical hMSC compositions, exhibiting enhanced therapeutic efficacy and superior safety profiles.

In at least one aspect, the presently described technology provides a composition comprising purified MSCs, wherein the composition comprises less than about 55 µg/mL residual BSA. In some embodiments related to this aspect of the present technology, the composition comprises less than about 42 µg/mL residual BSA. In some embodiments, the composition comprises less than about 25 µg/mL residual BSA. In some embodiments, the composition comprises less than about 13 µg/mL residual BSA. In some embodiments, the composition comprises less than about 10 µg/mL residual BSA. In other embodiments, the composition comprises between about 7 µg/mL residual BSA and about 15 µg/mL residual BSA. In still other embodiments, the composition comprises between about 8 µg/mL residual BSA and about 12 µg/mL residual BSA. In some embodiments related to this aspect of the present technology, the composition comprises purified MSCs, wherein the composition comprises less than about 50 µg/mL residual BSA; alternatively, less than about 45 µg/mL residual BSA; alternatively, less than about 40 µg/mL residual BSA; alternatively, less than about 35 µg/mL residual BSA; alternatively, less than about 30 µg/mL residual BSA; alternatively, less than about 25 µg/mL residual BSA; alternatively, less than about 20 µg/mL residual BSA; or alternatively, less than about 15 µg/mL residual BSA. Residual BSA resulting from published methods is generally reported to be about 30-700 µg BSA per $1 \times 10^6$ cells (Spees et al., *Mol Therapy*, 2004, 9: 747). As illustrated by the Examples below, the greater than 200-fold reduction in BSA between the published compositions and methods relative to the present technology represent a significant and surprisingly unexpected increase in the safety margin of MSC pharmaceutical compositions.

During incubation of MSCs in medium containing BSA, BSA may become associated with the MSC cell-surface. In order to accurately assess total BSA levels following incubation of MSCs in cell culture media supplemented with BSA, it is necessary to obtain a measurement that accounts for BSA in the supernatant as well as BSA that has become associated with the MSCs. For example, cells in an aliquot of the suspension may be lysed prior to measuring BSA levels. In this manner, total BSA levels, which comprises both free BSA and cell-associated BSA, can be obtained.

Also, some embodiments of the present technology provide a composition comprising purified MSCs, wherein the MSCs exhibit a $D_{90}$ between about 18 μm and about 30 μm. In some embodiments, the MSCs exhibit a $D_{90}$ between about 18 μm and about 25 μm. In some embodiments, the MSCs exhibit a $D_{90}$ between about 20 μm and about 25 μm. In some embodiments, the MSCs exhibit a $D_{90}$ less than about 30 μm; alternatively, less than about 25 μm; or alternatively, less than about 20 μm.

Some embodiments of the present technology relate to pharmaceutical MSC compositions, wherein the composition comprises less than about 55 μg/mL residual BSA and the MSCs exhibit a $D_{90}$ between about 18 μm and about 30 μm. In other embodiments related to this aspect of the present technology, the composition comprises less than about 42 μg/mL residual BSA and the MSCs exhibit a $D_{90}$ between about 18 μm and about 30 μm. In still other embodiments, the composition comprises less than about 25 μg/mL residual BSA and the MSCs exhibit a $D_{90}$ between about 18 μm and about 30 μm. In some embodiments, the composition comprises less than about 13 μg/mL residual BSA and the MSCs exhibit a $D_{90}$ between about 18 μm and about 30 μm. In some embodiments, the composition comprises less than about 10 μg/mL residual BSA and the MSCs exhibit a $D_{90}$ between about 18 μm and about 30 μm. In other embodiments, the composition comprises between about 7 μg/mL residual BSA and about 15 μg/mL residual BSA and the MSCs exhibit a $D_{90}$ between about 18 μm and about 30 μm. In still other embodiments, the composition comprises between about 8 μg/mL residual BSA and about 12 μg/mL residual BSA and the MSCs exhibit a $D_{90}$ between about 18 μm and about 30 μm. In some embodiments, the MSCs exhibit a $D_{90}$ between about 18 μm and about 25 μm and the composition comprises less than about 55 μg/mL residual BSA. In some embodiments, the MSCs exhibit a $D_{90}$ between about 20 μm and about 25 μm and the composition comprises less than about 55 μg/mL residual BSA. Some embodiments of the present technology provide a composition comprising purified MSCs, wherein the MSCs exhibit a $D_{90}$ between about 18 μm and about 25 μm and the composition comprises between about 8 μg/mL residual BSA and about 12 μg/mL residual BSA. In some embodiments, the MSCs exhibit a $D_{90}$ between about 20 μm and about 25 μm and the composition comprises between about 8 μg/mL residual BSA and about 12 μg/mL residual BSA.

As used herein, "aggregate" means the total of a plurality of individual cells together in a cluster grouped by one or more adhesive properties including aggregation, agglomeration and agglutination. As used herein, "aggregation" means the tendency for cells to aggregate. It was originally hypothesized, and later evidenced by experiments detailed in the Examples section of this patent application, that purified MSC populations exhibit a reduced tendency to form aggregates. Without being bound by theory, it is believed that these MSC aggregates do not efficiently disperse after administration and are of sufficient size to potentially cause fatal pulmonary emboli.

The present technology first recognized that the formation of an aggregate comprising MSCs can lead to pulmonary emboli. Increased amounts of xenogeneic substances can cause, among other things, increased cellular adhesion presumably due to certain xenogeneic substances interacting with membrane-bound sugars, proteins or other macro-molecules. Furthermore, current hMSC manufacturing practices result in increased cell surface substances, including sugars, proteins and other macromolecules (for example CD 105 and CD 166), present in the harvested hMSC compositions. Certain macromolecules, whether endogenous or exogenous, increase the adhesive characteristics of the MSCs. As the MSCs become more adhesive, they exhibit an increased tendency to aggregate with each other. Such aggregates may potentially increase the risk of a pulmonary embolism in recipients of hMSC pharmaceutical compositions. For example, BSA is believed to be capable of forming a non-covalent association with the MSC cell membrane both increasing the immunogenicity of the MSC and increasing the adhesive properties of the MSC. As such, the present technology identified and solved a previously unrecognized problem by providing compositions of MSCs with a reduced tendency to aggregate.

As such, techniques that process cells by simultaneously selecting for mass and size, such as centrifugal filtering, are preferred to techniques that serially select for mass then size, or vice versa. Some embodiments of the present technology comprise a pharmaceutical MSC composition consisting of a plurality of MSCs wherein the composition comprises one or more mesenchymal stem cell aggregates and the $D_{90}$ of said aggregates is less than about 150 μm. Some embodiments of the present technology comprise a pharmaceutical MSC composition consisting of a plurality of MSCs wherein the composition comprises one or more mesenchymal stem cell aggregates and the $D_{90}$ of said aggregates is less than about 100 μm. Some embodiments of the present technology comprise a pharmaceutical MSC composition consisting of a plurality of MSCs wherein the composition comprises one or more mesenchymal stem cell aggregates and the $D_{90}$ of said aggregates is less than about 50 prin. Indeed, some embodiments of the present technology comprise a pharmaceutical MSC composition consisting of a plurality of MSCs wherein the composition comprises no detectable mesenchymal stem cell aggregates.

Some embodiments of the present technology relate to pharmaceutical MSC compositions, wherein the composition comprises about 55 μg/mL residual BSA and wherein the composition comprises one or more mesenchymal stem cell aggregates and the $D_{90}$ of said aggregates is less than about 150 μm. In other embodiments related to this aspect of the present technology, the composition comprises less than about 42 μg/mL residual BSA and the composition comprises one or more mesenchymal stem cell aggregates, wherein the $D_{90}$ of said aggregates is less than about 150 μm. In still other embodiments, the composition comprises less than about 25 μg/mL residual BSA and the composition comprises one or more mesenchymal stem cell aggregates, wherein the $D_{90}$ of said aggregates is less than about 150 μm. In some embodiments, the composition comprises less than about 13 μg/mL residual BSA and the composition comprises one or more mesenchymal stem cell aggregates, wherein the $D_{90}$ of said aggregates is less than about 150 μm. In some embodiments, the composition comprises less than about 10 μg/mL residual BSA and the composition comprises one or more mesenchymal stem cell aggregates, wherein the $D_{90}$ of said aggregates is less than about 150 μm.

Some embodiments of the present technology comprise a pharmaceutical MSC composition consisting of a plurality of MSCs wherein the composition comprises one or more mesenchymal stem cell aggregates wherein no aggregate comprises more than 1,000 MSCs. Some embodiments of the present technology comprise a pharmaceutical MSC composition consisting of a plurality of MSCs wherein the composition comprises one or more mesenchymal stem cell aggregates wherein no aggregate comprises more than 750 MSCs. Some embodiments of the present technology comprise a pharmaceutical MSC composition consisting of a plurality of MSCs wherein the composition comprises one or more mesenchymal stem cell aggregates wherein no aggregate comprises more than 500 MSCs. Some embodiments of the present technology comprise a pharmaceutical MSC composition consisting of a plurality of MSCs wherein the composition comprises one or more mesenchymal stem cell aggregates wherein no aggregate comprises more than 200 MSCs. Some embodiments of the present technology comprise a pharmaceutical MSC composition consisting of a plurality of MSCs wherein the composition comprises one or more mesenchymal stem cell aggregates wherein no aggregate comprises more than 100 MSCs. Some embodiments of the present technology comprise a pharmaceutical MSC composition consisting of a plurality of MSCs wherein the composition comprises one or more mesenchymal stem cell aggregates wherein no aggregate comprises more than 50 MSCs. Some embodiments of the present technology comprise a pharmaceutical MSC composition consisting of a plurality of MSCs wherein the composition comprises one or more mesenchymal stem cell aggregates wherein no aggregate comprises more than 10 MSCs.

Following a period of incubation of hMSCs in culture medium, a number of molecules may be present in the culture medium, including extracellular and cell-membrane associated molecules. For example, such molecules may include xenogeneic substances, such as BSA and other molecules of non-human origin. Additionally, substances produced by the hMSCs themselves may be present in the culture medium following a period of incubation. For example, such molecules may include secreted proteins such as cytokines and growth factors as well as molecules expressed on the cell surface of the hMSCs. It may be desirable to purify hMSCs following a period of incubation in culture medium to remove molecules present in the culture medium, including extracellular and cell-membrane associated molecules. Such purification may reduce or prevent the tendency of the hMSCs to aggregate, reduce the size of any hMSC aggregates formed, or completely inhibit the formation of hMSC aggregates.

Without being bound by theory, it is not desirable to purify MSCs beyond the minimum safety thresholds disclosed herein as further purification may decrease the amount of adhesion molecules, such as integrins, that are expressed on the MSC cell surface. Such adhesion molecules are necessary for the MSCs to exert their therapeutic effect. Overly purified MSCs lack the quantity of adhesion molecules necessary to adhere to the target site within the body. In some embodiments, the systemically administered MSCs home to sites of inflammation within the body. These sites of inflammation exhibit higher expression profiles of adhesion molecules, and additionally induce conformational changes on adhesion molecules as a means to increase the affinity of MSCs to the inflamed tissue. If the MSCs lack the corresponding adhesion molecules, they do not adhere to the inflamed tissue and continue circulating until apoptosis. Thus, though it is desirable to reduce the expression of adhesion molecules on MSCs to the extent necessary to prevent aggregation, it is not desirable to reduce the expression of adhesion molecules on MSCs to such a degree that they lose their ability to adhere to an inflamed tissue site.

Xenogeneic substances, such as extracellular and cell surface membrane molecules, which are desirable to remove include serum proteins such as BSA and other non-human origin reagents for hMSC culturing such as porcine trypsin. In some embodiments of the present technology, the quantity of xenogeneic substances in the compositions comprising the culturally expanded hMSCs after purification is about 1 log less than the present in a comparable lot of un-purified culturally expanded hMSCs. In some embodiments, the quantity of xenogeneic substances after purification is about 2 log less than the present in a comparable lot comprising un-purified, culturally expanded hMSCs. In some embodiments, the quantity of xenogeneic substances after purification is about 3 log less than the present in a comparable lot comprising un-purified, culturally expanded hMSCs. In some embodiments, the quantity of xenogeneic substances after purification is about 4 log less than the present in a comparable lot comprising un-purified, culturally expanded hMSCs. In some embodiments, the quantity of xenogeneic substances after purification is about 5 log less than the quantity present in a comparable lot comprising un-purified, culturally expanded hMSCs. In some embodiments, the culturally expanded hMSC composition is substantially free of xenogeneic substances. In some embodiments, there are no detectable xenogeneic substances in composition comprising the culturally expanded hMSCs.

In further embodiments of the present technology, the quantity of xenogeneic substances in the compositions comprising the culturally expanded hMSCs after purification is about 10 to about 1,000-fold less than the quantity present in a comparable lot of un-purified, culturally expanded hMSCs. In some embodiments, the quantity of xenogeneic substances after purification is about 25 to about 750-fold less than the quantity present in a comparable lot comprising un-purified, culturally expanded hMSCs. In some embodiments, the quantity of xenogeneic substances after purification is about 50 to about 500-fold less than the quantity present in a comparable lot comprising un-purified, culturally expanded hMSCs. In some embodiments, the quantity of xenogeneic substances after purification is about 100 to about 300-fold less than the quantity present in a comparable lot comprising un-purified, culturally expanded hMSCs. In some embodiments, the quantity of xenogeneic substances after purification is about 200-fold less than the quantity present in a comparable lot comprising un-purified, culturally expanded hMSCs.

In other embodiments of the present technology, the quantity of BSA in the compositions comprising the culturally expanded hMSCs after purification is about 1 log less than the quantity present in a comparable lot of un-purified, culturally expanded hMSCs. In some embodiments, the quantity of BSA after purification is about 2 log less than the quantity present in a comparable lot comprising un-purified, culturally expanded hMSCs. In some embodiments, the quantity of BSA after purification is about 3 log less than the quantity present in a comparable lot comprising un-purified, culturally expanded hMSCs. In some embodiments, the quantity of BSA after purification is about 4 log less than the quantity present in a comparable lot comprising un-purified, culturally expanded hMSCs. In some embodiments, the quantity of BSA after purification is about 5 log less than the quantity present in a comparable lot comprising un-purified, culturally expanded hMSCs. Additionally, in some embodiments, the culturally expanded hMSC composition can be substantially free of BSA. In other embodiments, there is no detectable BSA in the composition comprising the culturally expanded hMSCs after purification.

In some embodiments of the present technology, the quantity of BSA in the compositions comprising the culturally expanded hMSCs after purification is about 10 to about 1,000-fold less than the quantity present in a comparable lot of un-purified, culturally expanded hMSCs. In some embodiments, the quantity of BSA after purification is about 25 to about 750-fold less than the quantity present in a comparable lot comprising un-purified, culturally expanded hMSCs. In some embodiments, the quantity of BSA after purification is about 50 to about 500-fold less than the quantity present in a comparable lot comprising un-purified, culturally expanded hMSCs. In some embodiments, the quantity of BSA after purification is about 100 to about 300-fold less than the quantity present in a comparable lot comprising un-purified, culturally expanded hMSCs. In some embodiments, the quantity of BSA after purification is about 200-fold less than the quantity present in a comparable lot comprising un-purified, culturally expanded hMSCs.

In some embodiments of the present technology, the quantity of extracellular nucleic acids in the compositions comprising the culturally expanded hMSCs after purification is about 1 log less than the quantity present in a comparable lot of un-purified, culturally expanded hMSCs. In some embodiments, the quantity of extracellular nucleic acids after purification is about 2 log less than the quantity present in a comparable lot comprising un-purified, culturally expanded hMSCs. In some embodiments, the quantity of extracellular nucleic acids after purification is about 3 log less than the quantity present in a comparable lot comprising un-purified, culturally expanded hMSCs. In some embodiments, the quantity of extracellular nucleic acids after purification is about 4 log less than the quantity present in a comparable lot comprising un-purified, culturally expanded hMSCs. In some embodiments, the quantity of extracellular nucleic acids after purification is about 5 log less than the quantity present in a comparable lot comprising un-purified, culturally expanded hMSCs. In other embodiments, the culturally expanded hMSC composition is substantially free of extracellular nucleic acids. In some embodiments, there are no detectable extracellular nucleic acids in the composition comprising the culturally expanded hMSCs after purification.

In some embodiments of the present technology, the quantities of BSA and extracellular nucleic acids in the compositions comprising the culturally expanded hMSCs after purification are each about 10 to about 1,000-fold less than the quantities present in a comparable lot of un-purified, culturally expanded hMSCs. In some embodiments of the present technology, the quantities of BSA and extracellular nucleic acids in the compositions comprising the culturally expanded hMSCs after purification are each about 25 to about 750-fold less than the quantities present in a comparable lot of un-purified, culturally expanded hMSCs. In some embodiments of the present technology, the quantities of BSA and extracellular nucleic acids in the compositions comprising the culturally expanded hMSCs after purification are each about 50 to about 500-fold less than the quantities present in a comparable lot of un-purified, culturally expanded hMSCs. In some embodiments of the present technology, the quantities of BSA and extracellular nucleic acids in the compositions comprising the culturally expanded hMSCs after purification are each about 100 to about 300-fold less than the quantities present in a comparable lot of un-purified, culturally expanded hMSCs. In some embodiments of the present technology, the quantities of BSA and extracellular nucleic acids in the compositions comprising the culturally expanded hMSCs after purification are each about 200-fold less than the quantities present in a comparable lot of un-purified, culturally expanded hMSCs.

Further, in some embodiments of the present technology, the quantity of extracellular nucleic acids in the compositions comprising the culturally expanded hMSCs after purification is about 10 to about 1,000-fold less than the quantity present in a comparable lot of un-purified, culturally expanded hMSCs. In some embodiments, the quantity of extracellular nucleic acids after purification is about 25 to about 750-fold less than the quantity present in a comparable lot comprising un-purified, culturally expanded hMSCs. In some embodiments, the quantity of extracellular nucleic acids after purification is about 50 to about 500-fold less than the quantity present in a comparable lot comprising un-purified, culturally expanded hMSCs. In some embodiments, the quantity of extracellular nucleic acids after purification is about 100 to about 300-fold less than the quantity present in a comparable lot comprising un-purified, culturally expanded hMSCs. In some embodiments, the quantity of extracellular nucleic acids after purification is about 200-fold less than the quantity present in a comparable lot comprising un-purified, culturally expanded hMSCs. In other embodiments, the quantity of extracellular nucleic acids after purification is about 1000-fold less than the quantity present in a comparable lot comprising un-purified, culturally expanded hMSCs; alternatively about 900-fold less; alternatively about 800-fold less; alternatively about 700-fold less; alternatively about 600-fold less; alternatively about 500-fold less; alternatively about 400-fold less; alternatively about 300-fold less; alternatively about 200-fold less; alternatively about 100-fold less; alternatively about 50-fold less; or alternatively about 25-fold less.

In some embodiments of the present technology, purified MSCs can be stored in an appropriate cryopreservation medium, for example a cryopreservation medium comprising DMSO. For example, in some embodiments, a pharmaceutical MSC composition may comprise MSCs and about 20% DMSO. In other embodiments, a pharmaceutical MSC composition may comprise MSCs and about 10% DMSO. In other embodiments, a pharmaceutical MSC composition may comprise MSCs and about 3.8% DMSO. In some embodiments, DMSO may be added to purified MSCs.

As used herein, the term "treating" refers to reversing, preventing, alleviating or inhibiting the progress of a disease, disorder or condition, or one or more symptoms of a disease, disorder or condition. As used herein, "treating" may also refer to decreasing the probability or incidence of the occurrence of a disease, disorder or condition in a mammal as compared to an untreated control population, or as compared to the same mammal prior to treatment. For example, as used herein, "treating" may refer to preventing a disease, disorder or condition, and may include delaying or preventing the onset of a disease, disorder or condition, or delaying or preventing the symptoms associated with a disease, disorder or condition. As used herein, "treating" may also refer to reducing the severity of a disease, disorder or condition or symptoms associated with such disease, disorder or condition prior to affliction with the disease, disorder or condition. Such prevention or reduction of the severity of a disease, disorder or condition prior to affliction relates to the administration of the composition of the present technology, as described herein, to a subject that is not at the time of administration afflicted with the disease, disorder or condition. As used herein "treating" may also further refer to preventing the recurrence of a disease, disorder or condition or of one or more symptoms associated with such disease, disorder or condition. The terms "therapy," "treatment," and "therapeutically," as used herein, refer to the act of treating as defined above.

The term "culture expanded" in reference to hMSCs means the passage of hMSCs one or more times under standard cell growth conditions in a minimum essential media (i) essentially free of cells of hematopoietic origin; and, (ii) supplemented with 10% FBS (by volume) resulting in an increased number of undifferentiated MSCs.

The term "pharmaceutical composition" refers to compositions at any stage of the manufacturing process, including the final pharmaceutically acceptable product and any in-process intermediates thereof.

Pharmaceutical compositions of the present technology may be produced by contacting a preparation including mesenchymal stem cells with a wash solution, agitating the preparation and the wash solution, and recovering purified mesenchymal stem cells.

In some embodiments, the wash solution can include an electrolyte solution comprising one or more ionic or ionizable compounds. Such compounds include, but are not limited to, sodium chloride, sodium gluconate, sodium acetate trihydrate, potassium chloride, and magnesium chloride, sodium phosphate and potassium phosphate. The wash solution may be comprised of a balanced electrolyte solution, the balanced electrolyte solution being composed of an appropriate concentration of sodium, potassium, chloride, or combinations thereof to maintain normal osmolality. Balanced electrolyte solutions include known salt solutions used in a variety of settings, including, for example, fluid electrolyte replacement therapy, washing tissues and cells, and diluents for cells and other factors.

In one embodiment, for example, the wash solution can be a nonpyrogenic isotonic solution, which, for every 100 ml of solution, there is approximately 526 mg of sodium chloride, 502 mg of sodium gluconate ($C_6H_{11}NaO_7$), 368 mg of sodium acetate trihydrate ($C_2H_3NaO_2.3H_2O$), 37 mg of potassium chloride, and 30 mg of magnesium chloride. One such commercially available isotonic electrolyte solution is sold as PlasmaLyte A, a product of Baxter Healthcare Corporation, Deerfield, Ill.

In another embodiment, the mesenchymal stem cells are washed in an apparatus that includes, for example, a cell source bag, a wash solution bag, a recirculation wash bag, a spinning membrane filter having inlet and outlet ports, a filtrate bag, a mixing zone, an end product bag for the washed cells, and appropriate tubing. The apparatus may be a closed system, thereby reducing the potential for contamination.

Unwashed MSCs from the cell source bag can be mixed with the wash solution in the centrifugal filtration device. The resulting suspension of mesenchymal stem cells in wash solution then is fed to the spinning membrane filter through an inlet port. A filtrate comprising wash solution is withdrawn from the spinning membrane filter through a first outlet port, and a concentrated suspension of MSCs is withdrawn from the spinning membrane filter through a second outlet port, and fed into the recirculation wash bag. The MSCs then are withdrawn from the recirculation wash bag, mixed with additional wash solution, and sent again to the spinning membrane filter. When recirculation washing of the MSCs is completed, the washed MSCs are sent to the product bag.

FIG. 1 shows an exemplary apparatus for washing or purifying MSCs. An example of such an apparatus is further described in U.S. Pat. No. 6,251,295. The apparatus, as noted in U.S. Pat. No. 6,251,295, may include, for example, a recirculation bag 5 having top port 2 and bottom port 1; a spinning membrane filter 6 having an inlet port 11 for a diluted suspension of MSCs, an outlet port 14 for a concentrated suspension of MSCs, and an outlet port 24 for filtrate; and filtrate bag 30 having an inlet port 29. It may also include one or more of a washed cell bag 46 having an outlet port 47, an unwashed cell bag 44 having an outlet port 45, and a wash solution bag 7 having an outlet port 21. Top port 2 of bag 5 is connected by tubing 8 to connector 49. Port 21 of wash solution bag 7 is connected by tubing 15 to Y-connector 55 and the latter is connected by tubing 20 carrying clamp C1 to connector 49. Port 45 of unwashed cell bag is connected by tubing 43 carrying clamp C3 to Y-connector 53 and then by tubing 51 to connector 49. Connector 49 serves as a mixing zone for unwashed cells in wash solution from bag 44, recirculating cells in wash solution from bag 5 and wash solution from bag 7. Connector 49 is connected by tubing 10 to inlet port 11 of spinning membrane filter 6. Filtrate outlet port 24 of spinner 6 is connected by tubing 23 to Y-connector 54 and by tubing 26 to the inlet port 29 of filtrate bag 30. Connector 55 is connected by tubing 52 carrying clamp C2 to connector 54. Connector 54 is connected by tubing 41 to pressure transducer 50. Outlet port 14 of spinner 6 is connected by tubing 13 to the bottom port 1 of bag 5. Y-connector 53 is connected by tubing 48 carrying clamp C4 to inlet port 47 of washed cell bag 46.

During recirculation washing, a suspension of MSCs in wash solution is withdrawn from the bag 5 through the top port 2 and flows through tubing 8 to mixing zone 49. A suspension of MSCs are withdrawn from bag 44 through port 45 and (with clamp C3 open and clamp C4 closed) through tubing 43 to Y-connector 53 and then through tubing 51 to mixing zone 49 by the transfer pump P2. Wash solution is withdrawn from bag 7 through port 21 and tubing 15 to connector 55 by the buffer pump P2. With clamp C1 open, wash solution flows through tubing 20 to mixing zone 49. A suspension of MSCs in wash solution flows from mixing zone 49 through tubing 10 to inlet port 11 of spinner 6. A concentrated suspension of MSCs in wash solution flows through outlet port 14 of spinner 6 through tubing 13 and inlet port 1 into bag 5 by recirculation pump P3. Filtrate flows through outlet port 24 in spinner 6 and tubing 23 to connector 54 and, with clamp C2 closed, through tubing 26 and inlet port 29 into filtrate bag 30 by pump P4. Recirculation washing is continued until the desired amount of target component has been removed from the MSCs. Clamps C1, C2 and C3 then are closed, clamp C4 is opened, and the direction of pump P1 is reversed, so that the suspension of washed MSCs flows from bag 5 through tubing 8, 51 and 48 and port 47 into washed cell bag 46. The lines, bag, and spinner then are rinsed by closing clamps C1 and C3, opening clamps C4 and C2, and pumping buffer with pump P2 in series with pumps P1 and P3 to rinse the spinner, bag and tubing.

The purification process may include sequential or simultaneous centrifugation and filtering.

Centrifugal filtering devices comprising spinning membranes, have been developed to remove platelets and antibodies from blood products. Exemplary centrifugal filtering devices include those disclosed in, for example, U.S. Pat. Nos. 5,034,135; 5,053,121; 5,234,608; 5,536,475; and, 6,251,295, each of which are independently incorporated by reference in their entirety.

In one or more embodiments, the spinning membrane filter has a pore size of from about 3 μm to about 7 μm. In another embodiment, the membrane filter has a pore size of about 4 μm.

In some embodiments of the present technology, the post-wash viability of the cells is greater than about 60%. In other embodiments, the post-wash viability of the cells is greater than about 70%. In further embodiments, the post-wash viability of the cells is greater than about 80%. In still further embodiments, the post-wash viability of the cells is greater than about 90%. In further embodiments, the post-wash viability of the cells is greater than about 95%.

Certain embodiments of the present technology relate to purified pharmaceutical MSC compositions, wherein the composition comprises about 55 µg/mL residual BSA; wherein the composition comprises one or more mesenchymal stem cell aggregates and the $D_{90}$ of said aggregates is less than about 150 µm; and wherein the post-purification viability of the MSCs is greater than about 80%. In other embodiments related to this aspect of the present technology, the composition comprises less than about 42 µg/mL residual BSA; the composition comprises one or more mesenchymal stem cell aggregates and the $D_{90}$ of said aggregates is less than about 150 µm; and the post-purification viability of the MSCs is greater than about 80%. In still other embodiments, the composition comprises less than about 25 µg/mL residual BSA; the composition comprises one or more mesenchymal stem cell aggregates and the $D_{90}$ of said aggregates is less than about 150 µm; and the post-purification viability of the MSCs is greater than about 80%. In some embodiments, the composition comprises less than about 13 µg/mL residual BSA; the composition comprises one or more mesenchymal stem cell aggregates and the $D_{90}$ of said aggregates is less than about 150 µm; and the post-purification viability of the MSCs is greater than about 80%. In some embodiments, the composition comprises less than about 10 µg/mL residual BSA; the composition comprises one or more mesenchymal stem cell aggregates and the $D_{90}$ of said aggregates is less than about 150 µm; and the post-purification viability of the MSCs is greater than about 80%. In some embodiments, the composition comprises between about 7 µg/mL residual BSA and about 15 µg/mL residual BSA; the composition comprises one or more mesenchymal stem cell aggregates and the $D_{90}$ of said aggregates is less than about 150 µm; and the post-purification viability of the MSCs is greater than about 80%. In other embodiments, the composition comprises between about 8 µg/mL residual BSA and about 12 µg/mL residual BSA; the composition comprises one or more mesenchymal stem cell aggregates and the $D_{90}$ of said aggregates is less than about 150 µm; and the post-purification viability of the MSCs is greater than about 80%.

Certain embodiments of the present technology relate to purified pharmaceutical MSC compositions, wherein the composition comprises about 55 µg/mL residual BSA; wherein the composition comprises one or more mesenchymal stem cell aggregates and the $D_{90}$ of said aggregates is less than about 150 µm; and wherein the post-purification viability of the MSCs is greater than about 70%. In other embodiments related to this aspect of the present technology, the composition comprises less than about 42 µg/mL residual BSA; the composition comprises one or more mesenchymal stem cell aggregates and the $D_{90}$ of said aggregates is less than about 150 µm; and the post-purification viability of the MSCs is greater than 70%. In still other embodiments, the composition comprises less than about 25 µg/mL residual BSA; the composition comprises one or more mesenchymal stem cell aggregates and the $D_{90}$ of said aggregates is less than about 150 µm; and the post-purification viability of the MSCs is greater than 70%. In some embodiments, the composition comprises less than about 13 µg/mL residual BSA; the composition comprises one or more mesenchymal stem cell aggregates and the $D_{90}$ of said aggregates is less than about 150 µm; and the post-purification viability of the MSCs is greater than 70%. In some embodiments, the composition comprises less than about 10 µg/mL residual BSA; the composition comprises one or more mesenchymal stem cell aggregates and the $D_{90}$ of said aggregates is less than about 150 µm; and the post-purification viability of the MSCs is greater than 70%. In some embodiments, the composition comprises between about 7 residual BSA and about 15 µg/mL residual BSA; the composition comprises one or more mesenchymal stem cell aggregates and the $D_{90}$ of said aggregates is less than about 150 µm; and the post-purification viability of the MSCs is greater than 70%. In other embodiments, the composition comprises between about 8 µg/mL residual BSA and about 12 µg/mL residual BSA; the composition comprises one or more mesenchymal stem cell aggregates and the $D_{90}$ of said aggregates is less than about 150 µm; and the post-purification viability of the MSCs is greater than 70%.

The presently described technology now will be described with respect to the following example; however, the scope of the present technology is not intended to be limited thereby. It is to be understood that the scope of the present technology is not to be limited to the specific embodiments described above. The technology may be practiced other than as particularly described and still be within the scope of the claims.

EXAMPLE 1

Thresholds for Residual Xenogeneic Proteins in Compositions for IV Administration In documenting Absorption, Distribution, Metabolism, Excretion and Toxicity ("ADMET") properties of MSC pharmaceutical compositions, sporadic and unpredictable deaths in rodent test populations receiving MSCs were reported. In studying a number of parameters, the residual quantity of xenogeneic proteins, residual quantity of other debris resulting from the expansion in media, and degree of cell aggregation were identified as, and later proven to be, a significant contributing factor to adverse events observed in pre-clinical experiments.

The present technology uncovers and appreciates that though clinical reactivity thresholds are established for oral administration of antigens, thresholds for IV exposure to antigens remain unknown. As such, the present technology recognized that the problem of understanding thresholds for IV exposure to antigens needed to be solved before a safe MSC pharmaceutical composition and manufacturing process therefore could be designed. To understand adverse reactions associated with cellular and animal-derived products, such as anaphylaxis and serum sickness like disease, in the context of IV administration of compositions comprising MSCs, an animal model was employed to determine the antigenic potential of xenogeneic residuals.

Ovalbumin ("OVA") was selected as a representative xenogeneic protein as it is structurally related to BSA, significantly more immunogenic than BSA and trypsin, and documented in a significant number of published reports. BSA has significantly lower allergenic potential in comparison to OVA (Hilton J. et al., Food Chem Toxicol, 1997, 35:1209).

The OVA was administered by systemic, non-mucosal, intra-peritoneal (IP) injection as this route was deemed most relevant to IV administration. It has been shown IP and IV routes of antigen administration in animals results in similar outcome (Shepard et al., Infection and Immunity, 1982, 38: 673).

For calculation of BSA and trypsin threshold tolerances in an MSC pharmaceutical composition, the lowest cumulative dose of OVA that did not trigger a detectable IgE response was selected. The lowest cumulative OVA dose that does not trigger sensitization when delivered IP is 10 µg/mouse, corresponding to 500 µg/kg based on average 20 g mouse body weight. Thus, a safe cumulative dose of animal protein residuals in MSC pharmaceutical compositions for non-susceptible patients receiving treatments with MSCs is 500 µg/kg. In accordance with that safety limit, a 100 kg patient could safely be administered an MSC pharmaceutical composition comprising less than about 50 mg of animal protein; a 40 kg patient could safely be administered an MSC pharmaceutical composition comprising less than about 20 mg of animal protein; or, a 5 kg pediatric patient could safely be administered an MSC pharmaceutical composition comprising less than about 2.5 mg of animal protein.

Having recognized and solved the problem associated with threshold IV exposure to antigens, parameters for a manufacturing process suitable for producing safe MSC pharmaceutical composition could now be implemented. For therapy consisting of 2 IV infusions of $8 \times 10^6$ MSCs/kg body weight per treatment, a threshold for residual BSA and trypsin per MSC pharmaceutical composition (830 µg corresponding to 55 µg/mL) was calculated as depicted in Table 1.

C. After 8 days, non adherent cells were removed and remaining cells detached with 0.05% porcine trypsin and 0.53 mM EDTA. Adherent cells were re-plated at 2,000 cells/cm^2. Two (2) subsequent passages were performed at 4 day intervals.

After expansion, an aliquot of the cell suspension was obtained to assess residual BSA levels. The cells in the aliquot were lysed prior to performing an ELISA to determine residual BSA, the results of which are exhibited in Table 2. The MSCs in α-MEM were then frozen in cryovials containing a known number of MSCs.

To prepare dosing formulations for each concentration, the estimated final suspension volume was calculated from the desired cell concentration and the estimated cell count per cryovial assuming 90% viability of the MSCs. The amount of vehicle needed to achieve the estimated final suspension volume was transferred into a conical tube. Cryovials containing the population of MSCs were transferred from liquid nitrogen storage to a water bath until thawed to semi-liquid. Approximately 0.5 mL of vehicle was transferred to each cryovial to facilitate complete thawing. The population of MSCs was

TABLE 1

Thresholds for residual xenogeneic substances in an MSC pharmaceutical composition for IV administration

| Patient body weight | Cumulative dose for residuals | Cells/kg per dose | No. of hMSC treatments/ infusions | Cell dose per infusion ($\times 10^6$) | Cell dose per treatment - 2 infusions ($\times 10^6$) | Cumulative cell dose - 3 treatments ($\times 10^6$) | Total No. of Final Product bags | Allowed residuals per Final Product bag (mg) | Allowed amount of residuals (ug/ml) |
|---|---|---|---|---|---|---|---|---|---|
| 5 kg | 2.5 mg | $8 \times 10^6$ | 3/6 | 40 | 80 | 240 | 2.5-3 | 0.83-1 | 55.3-66.7 |
| 40 kg | 20 mg | $8 \times 10^6$ | 3/6 | 320 | 640 | 1920 | 19-20 | 1-1.05 | 66.7-70 |
| 100 kg | 50 mg | $8 \times 10^6$ | 3/6 | 800 | 1600 | 4800 | 48 | 1.04 | 69.3 |
| 300 kg | 150 mg | $8 \times 10^6$ | 3/6 | 2400 | 4800 | 14400 | 144 | 1.04 | 69.3 |

EXAMPLE 2

Purity of the MSC Pharmaceutical Composition

To evaluate the potential effects of culturally-expanded MSCs on the potential change in pulmonary function as a function of the purity of the MSC pharmaceutical composition, a pharmaceutical hMSC composition consisting essentially of: 1) a population of MSCs; and, 2) a vehicle consisting of 85% PlasmaLyteA, 10% DMSO, and 5% FBS (by volume) was prepared.

The experiments noted in this Example 2 were conducted in accordance with the U.S. Food & Drug Administrations Good Laboratory Practice Regulations as codified in 21 C.F.R. 58, except that there was no documentation of the strength, purity, and composition of the Plasma-Lyte A component of the vehicle (which was purchased as a sterile component). The manufacture of the test article was conducted in accordance with Good Manufacturing Practices. The species selection and number of animals tested was supported by the FDA guidelines for Expanded Acute Studies, ICH Harmonised Tripartite Guidelines, FDA Guidance for Human Somatic Cell Therapy and Gene Therapy, and generally accepted procedures for pre-clinical pharmaceutical testing.

A population of rat bone marrow-derived MSCs was cultured as follows. Harvested marrow was flushed with Hank's buffered solution. Cells were pooled, counted, and centrifuges at 100 g for 10 min. Cells were then plated in flasks at $120 \times 10^6$ cells/cm^2 in 10% FBS, 45% Ham's F-12, 45% alpha-Minimum Essential Medium ("α-MEM") supplemented with 100 U/ml penicillin G and 100 ug/ml streptomycin sulfate. Flasks were incubated in 10% CO_2 at 37 deg.

transferred to the conical tube at which time the population was purified by either: (A) Basic Centrifugation; or, (B) Centrifugal Filtering.

(A) Basic Centrifugation. The cell/vehicle suspension was centrifuged for approximately 10 minutes at 500 g-force at 4 degrees Celsius (1,480-1540 3,000 RPM in a Beckman GS-6R rotor GH 3.8). The supernatant was removed and retained in a separate vial. The pelleted cells were resuspended with vehicle if necessary. The MSCs were counted and the viability was confirmed. Based on the total cell count, the amount of vehicle needed to achieve the desired final suspension volume was added to provide an hMSC pharmaceutical composition. The compositions purified by basic centrifugation were assayed by ELISA to determine residual BSA, the results of which are exhibited in Table 2.

(B) Centrifugal Filtering. The cell/vehicle suspension was washed for approximately 25 minutes at room temperature in a Cytomate Cell Processing System (as sold by Baxter in 2007) having a spinning membrane filter with a pore size of about 4 µm and using a Residual Fold Reduction (RFR) setting of 150. The MSCs were counted and the viability was confirmed. The compositions purified by centrifugal filtering were assayed with an ELISA assay to determine residual BSA, the results of which are exhibited in Table 3.

Based on the total cell count, the amount of vehicle needed to achieve the desired final suspension volume was added to provide an hMSC pharmaceutical composition. All hMSC pharmaceutical compositions were prepared less than 4 hours prior to administration. Animals were dosed via femoral catheter. As exhibited in Table 2 below, MSC pharmaceutical compositions purified by centrifugal filtering demonstrated no deaths while MSC pharmaceutical compositions purified by traditional centrifugation techniques resulted in 80% mortality. The causes of death were determined to be pulmonary emboli.

TABLE 2

Change in Pulmonary Function as a Function of the Purity of the MSC Pharmaceutical Composition

| | Group A | Group B | Group C | Group D | Group E |
|---|---|---|---|---|---|
| Number of Rats | 10 | 10 | 10 | 10 | 10 |
| Number of Cells Infused | $37.5 \times 10^6$ cells/kg | $37.5 \times 10^6$ cells/kg | $75 \times 10^6$ cells/kg | Zero, Saline only | Zero, Vehicle only |
| Purification Method | Basic Centrifugation | Centrifugal Filtering | Centrifugal Filtering | n/a | n/a |
| Post-wash Viability (before infusion) | 68.7% | 67.8% | 67.8% | n/a | n/a |
| Result | 7 rats died immediately after infusion; 1 died with 24 hrs. of infusion; 2 survived to planned necroscopy | No Unscheduled deaths | No Unscheduled deaths | No Unscheduled deaths | No Unscheduled deaths |

Of the several parameters subsequently studied, a second analysis comparing the amount of residual BSA present in a MSC composition to the No Observed Adverse Events Level ("NOAEL") limits, the results of which are exhibited in Table 3, provided the most surprising results.

TABLE 3

Correlation of Residual BSA: NOAEL

| Process Method | BSA residual (μg/mL) | No Observed Adverse Events Level | Rat Number |
|---|---|---|---|
| No processing | 26.00 | Not Determined | Not Determined |
| Basic Centrifugation | 1.29 | $4 \times 10^6$ cells/kg | 10 |
| Centrifugal Filtering | 0.13 | $40 \times 10^6$ cells/kg | 120 |

Of the 10 rats infused with an MSC composition purified by basic centrifugation referenced in Table 2, 7 rats died immediately after dosing, 1 rat died the day following dosing, and 2 rats survived 14 days to planned terminal necropsy. Prior to proceeding with further pre-clinical or clinical phase studies, there was a desire to increase the safety margin provided by MSC compositions purified by basic centrifugation.

An additional toxicology test was performed on MSC pharmaceutical compositions purified by centrifugal filtration. In this experiment, 120 rats were administered $10 \times 10^6$ cells/kg, $40 \times 10^6$ cells/kg, or $75 \times 10^6$ cells/kg. Of the 120 rats studied there were only 2 animal deaths during the study. Further bolstering the fully binary results (i.e. full survival or full fatality) of this experiment, it was also noted that animals receiving centrifugally filtered MSC pharmaceutical compositions demonstrated almost no clinical symptoms, even at a dose level twice as high ($75 \times 10^6$ cells/kg) as was fatal when purified by basic centrifugation.

After this experiment was conducted, all cell processing protocols were adapted for centrifugal filtering.

As exhibited in Table 3, MSC compositions purified by basic centrifugation were found to have 1.29 μg/mL residual BSA that resulted in a NOAEL of $3 \times 10^6$ cells/kg. By comparison, MSC compositions purified by centrifugal filtering were found to have 0.13 μg/mL residual BSA that resulted in a NOAEL of $40 \times 10^6$ cells/kg thus exhibiting an approximately 10-fold increase in safety margins. As the approximately 20-fold decrease in residual BSA between unpurified MSC compositions and MSC compositions purified by centrifugation did not increase the NOAEL limit to a clinically significant dose (e.g. $10 \times 10^6$ cells/kg, $40 \times 10^6$ cells/kg, or $75 \times 10^6$ cells/kg) and still resulted in full mortality at $37.5 \times 10^6$ cells/kg, it was quite surprising to observe that a further 10-fold increase in purity would increase the NOAEL limit an additional 1 log and also result in full survival of the tested animal population.

In analyzing bovine and porcine residuals in combination centrifugal filtering reduced the residual level of animal proteins approximately 1,000-fold relative to basic centrifugation. This 1,000-fold reduction increased the maximum tolerated dose for bolus infusion from $20 \times 10^6$ cells/kg to $65 \times 10^6$ cells/kg.

Figure 2:
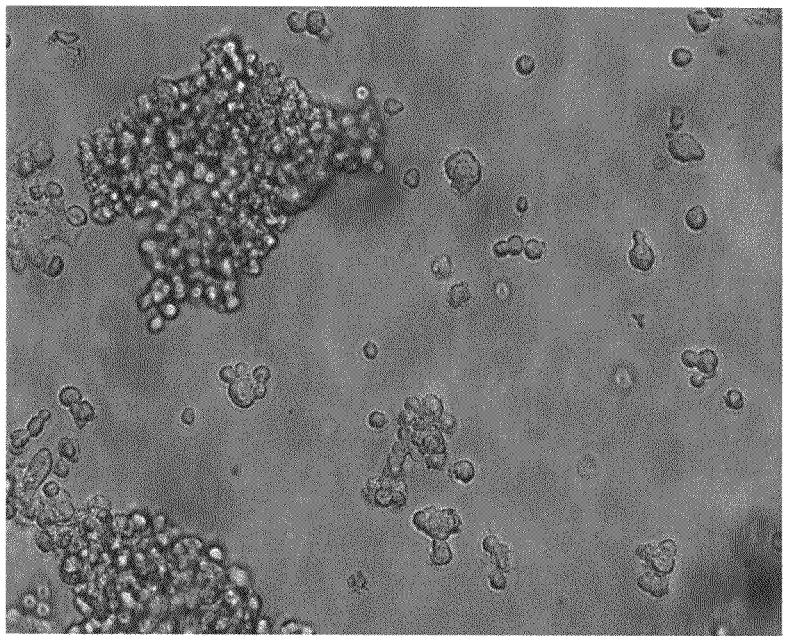
FIG. 2 is a photograph (10× magnification) of an unpurified MSC composition.
Figure 3:
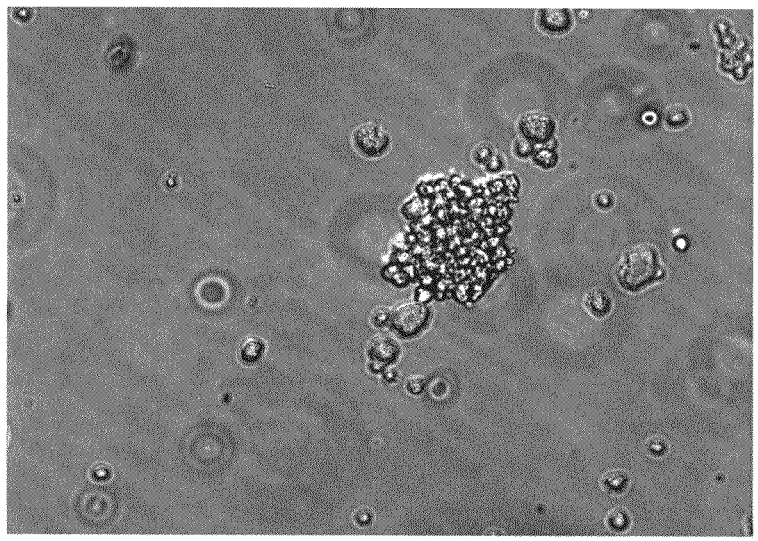
FIG. 3 is a photograph (10× magnification) of an MSC composition purified by centrifugation.
Figure 4:
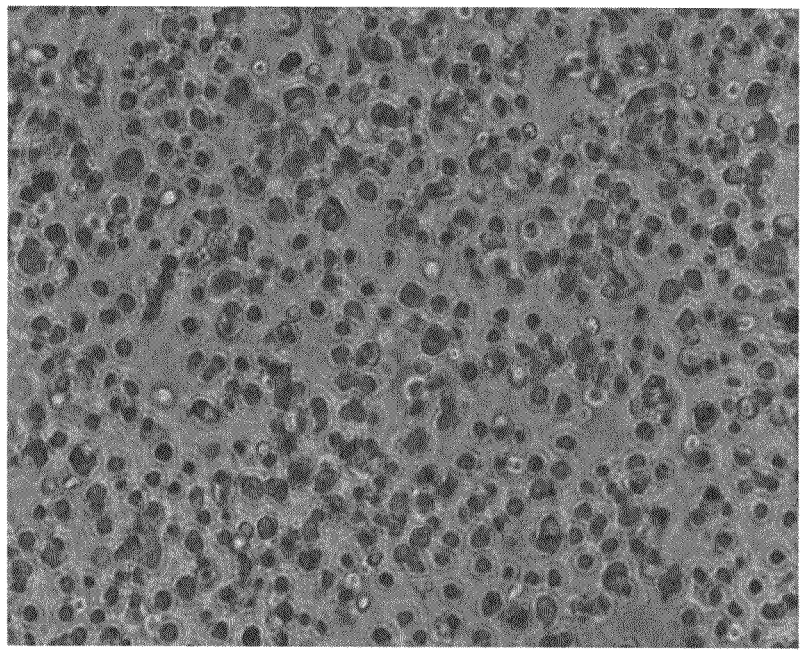
FIG. 4 is a photograph (10× magnification) of an MSC composition purified by centrifugal filtration.

Photographs taken under 10× magnification of an unpurified MSC composition (FIG. 2), an MSC composition purified by centrifugation (FIG. 3), and an MSC composition purified by centrifugal filtration (FIG. 4) exhibit the reduced tendency of MSC compositions purified by centrifugal filtration to form aggregates.

Additional embodiments of the presently described technology now will be described; however, the scope of the present technology is not intended to be limited thereby. It is to be understood that the scope of the present technology is not to be limited to the specific embodiments described below. The technology may be practiced other than as particularly described and still be within the scope of the appended claims. Additional embodiments of the present technology include:

A pharmaceutically acceptable composition comprising purified mesenchymal stem cells, wherein the composition comprises one or more mesenchymal stem cell aggregates and the $D_{90}$ of said aggregates is less than about 150 μm.

The pharmaceutically acceptable composition of Paragraph [00095], wherein the $D_{90}$ of said aggregates is less than about 100 μm.

The pharmaceutically acceptable composition of Paragraph [00096], wherein the $D_{90}$ of said aggregates is less than about 50 μm.

The pharmaceutically acceptable composition of any one of Paragraphs [00095]-[00097], wherein viability of the purified mesenchymal stem cells is greater than about 70%.

The pharmaceutically acceptable composition of Paragraph [00098], wherein viability of the purified mesenchymal stem cells is greater than about 80%.

The pharmaceutically acceptable composition of any one of Paragraphs [00095]-[00099], further comprising dimethyl sulfoxide (DMSO).

The pharmaceutically acceptable composition of Paragraph [000100], comprising about 10% DMSO.

The pharmaceutically acceptable composition of Paragraph [000100], comprising about 3.8% DMSO.

A pharmaceutically acceptable composition comprising purified mesenchymal stem cells, wherein the composition comprises less than about 55 µg/mL residual bovine serum albumin and wherein the mesenchymal stem cells exhibit a $D_{90}$ between about 18 µm and about 30 µm.

The composition of Paragraph [000103], wherein the composition comprises less than about 42 µg/mL residual bovine serum albumin.

The composition of Paragraph [000104], wherein the composition comprises less than about 25 µg/mL residual bovine serum albumin.

The composition of Paragraph [000105], wherein the composition comprises less than about 13 µg/mL residual bovine serum albumin.

The composition of Paragraph [000106], wherein the composition comprises less than about 10 µg/mL residual bovine serum albumin.

The composition of Paragraph [000103], wherein the composition comprises between about 7 µg/mL and about 15 µg/mL residual bovine serum albumin.

The composition of Paragraph [000108], wherein the composition comprises between about 8 µg/mL and about 12 µg/mL residual bovine serum albumin.

The composition of any of Paragraphs [000103]-[000109], wherein the mesenchymal stem cells exhibit a $D_{90}$ between about 18 µm and about 25 µm.

The composition of Paragraph [000110], wherein the mesenchymal stem cells exhibit a $D_{90}$ between about 20 µm and about 25 µm.

The composition of any of Paragraphs [000103]-[000111], wherein the mesenchymal stem cells are culturally expanded in a media comprising bovine serum albumin.

The composition of any of Paragraphs [000103]-[000111], wherein the mesenchymal stem cells are culturally expanded in media comprising animal serum.

The composition of Paragraph [000113], wherein the animal serum is human serum.

The composition of Paragraph [000113], wherein the animal serum is non-human serum.

The composition of Paragraph [000115], wherein the non-human serum is bovine serum.

The composition of Paragraph [000115], wherein the non-human serum is porcine serum.

The composition of any one of Paragraphs [000103]-[000117], wherein viability of the purified mesenchymal stem cells is greater than about 70%.

The composition of Paragraph [000118], wherein viability of the purified mesenchymal stem cells is greater than about 80%.

The composition of any one of Paragraphs [000103]-[000119], further comprising dimethyl sulfoxide (DMSO).

The pharmaceutically acceptable composition of Paragraph [000120], comprising about 10% DMSO.

The pharmaceutically acceptable composition of Paragraph [000120], comprising about 3.8% DMSO.

A process for preparing a purified mesenchymal stem cell composition comprising the steps of:
(i) Obtaining a preparation that contains ex vivo cultured mesenchymal stem cells;
(ii) Contacting the preparation with a wash solution to create a mixture;
(iii) Agitating the mixture with a centrifugal filtration device; and,
(iv) Recovering a purified mesenchymal stem cell composition.

The process of Paragraph [000123], wherein said ex vivo cultured mesenchymal stem cells are cultured in media comprising bovine serum albumin.

The process of Paragraph [000123], wherein said ex vivo cultured mesenchymal stem cells are cultured in media comprising animal serum.

The process of Paragraph [000125], wherein the animal serum is human serum.

The process of Paragraph [000125], wherein the animal serum is non-human serum.

The process of Paragraph [000127], wherein the non-human serum is bovine serum.

The process of Paragraph [000127], wherein the non-human serum is porcine serum.

The process of any one of Paragraphs [000123]-[000129], wherein said purified mesenchymal stem cell composition comprises less than about 55 µg/mL residual bovine serum albumin.

The process of Paragraph [000130], wherein the purified mesenchymal stem cell composition comprises less than about 42 µg/mL residual bovine serum albumin.

The process of Paragraph [000131], wherein the purified mesenchymal stem cell composition comprises less than about 25 µg/mL residual bovine serum albumin.

The process of Paragraph [000132], wherein the purified mesenchymal stem cell composition comprises less than about 13 µg/mL residual bovine serum albumin.

The process of Paragraph [000133], wherein the purified mesenchymal stem cell composition comprises less than about 10 µg/mL residual bovine serum albumin.

The process of any one of Paragraphs [000123]-[000129], wherein said purified mesenchymal stem cell composition comprises between about 7 µg/mL and about 15 µg/mL residual bovine serum albumin.

The process of Paragraph [000135], wherein said purified mesenchymal stem cell composition comprises between about 8 µg/mL and about 12 µg/mL residual bovine serum albumin.

The process of any one of Paragraphs [000123]-[000136], further comprising adding DMSO to said purified mesenchymal stem cell composition.

The process of Paragraph [000137], wherein said composition comprises about 10% DMSO.

The process of Paragraph [000137], wherein said composition comprises about 3.8% DMSO.

A purified mesenchymal stem cell composition obtained by the process of any one of Paragraphs [000123]-[000139].

A purified mesenchymal stem cell composition produced by:
(i) Culturing mesenchymal stem cells in media comprising serum;
(ii) Obtaining a preparation that comprises said mesenchymal stem cells;
(iii) Contacting the preparation with a wash solution to create a mixture;
(iv) Agitating the mixture with a centrifugal filtration device; and,
(v) Recovering a purified mesenchymal stem cell composition.

The composition of Paragraph [000141], wherein the mesenchymal stem cells exhibit a $D_{90}$ between about 18 µm and about 30 µm.

The composition of Paragraph [000142], wherein the mesenchymal stem cells exhibit a $D_{90}$ between about 18 µm and about 25 µm.

The composition of Paragraph [000143], wherein the mesenchymal stem cells exhibit a $D_{90}$ between about 20 μm and about 25 μm.

The composition of any one of Paragraphs [000141]-[000144], wherein said serum is bovine serum and said composition comprises less than about 55 μg/mL residual bovine serum albumin.

The composition of Paragraph [000145], wherein said composition comprises less than about 42 μg/mL residual bovine serum albumin.

The composition of Paragraph [000146], wherein said composition comprises less than about 25 μg/mL residual bovine serum albumin.

The composition of Paragraph [000147], wherein said composition comprises less than about 13 μg/mL residual bovine serum albumin.

The composition of Paragraph [000148], wherein said composition comprises less than about 10 μg/mL residual bovine serum albumin.

The composition of any one of Paragraphs [000141]-[000144], wherein said serum is bovine serum and said composition comprises between about 7 μg/mL and about 15 μg/mL residual bovine serum albumin.

The composition Paragraph [000150], wherein said composition comprises between about 8 μg/mL and about 12 μg/mL residual bovine serum albumin.

A pharmaceutically acceptable composition comprising purified mesenchymal stem cells, wherein said mesenchymal stem cells are culturally expanded in media containing bovine serum albumin; and wherein said composition comprises less than about 55 μg/mL residual bovine serum albumin.

The composition of Paragraph [000152], wherein said composition comprises less than about 42 μg/mL residual bovine serum albumin.

The composition of Paragraph [000153], wherein said composition comprises less than about 25 μg/mL residual bovine serum albumin.

The composition of Paragraph [000154], wherein said composition comprises less than about 13 μg/mL residual bovine serum albumin.

The composition of Paragraph [000155], wherein said composition comprises less than about 10 μg/mL residual bovine serum albumin.

The composition of Paragraph [000152], wherein said composition comprises between about 7 μg/ml and about 15 μg/ml residual bovine serum albumin.

The composition of Paragraph [000157], wherein said composition comprises between about 8 μg/ml and about 12 μg/mL residual bovine serum albumin.

A pharmaceutically acceptable composition comprising purified mesenchymal stem cells, wherein the composition comprises less than about 55 μg/mL residual bovine serum albumin.

The composition of Paragraph [000159], wherein the composition comprises less than about 42 μg/mL residual bovine serum albumin.

The composition of Paragraph [000160], wherein the composition comprises less than about 25 μg/mL residual bovine serum albumin.

The composition of Paragraph [000161], wherein the composition comprises less than about 13 μg/mL residual bovine serum albumin.

The composition of Paragraph [000162], wherein the composition comprises less than about 10 μg/mL residual bovine serum albumin.

The composition of Paragraph [000159], wherein the composition comprises between about 7 μg/mL and about 15 μg/mL residual bovine serum albumin.

The composition of Paragraph [000164], wherein the composition comprises between about 8 μg/mL and about 12 μg/mL residual bovine serum albumin.

The composition of any one of Paragraphs [000159]-[000165], further comprising DMSO.

The composition of Paragraph [000166], comprising about 10% DMSO.

The composition of Paragraph [000166], comprising about 3.8% DMSO.

A pharmaceutically acceptable composition comprising purified mesenchymal stem cells, wherein the composition comprises one or more mesenchymal stem cell aggregates and the $D_{90}$ of said aggregates is less than about 150 μm; wherein the composition comprises between about 8 μg/mL and about 12 μg/mL residual bovine serum albumin; and wherein the mesenchymal stem cells exhibit a $D_{90}$ between about 18 μm and about 30 μm.

The pharmaceutically acceptable composition of Paragraph [000169], wherein the $D_{90}$ of said aggregates is less than about 100 μm.

The pharmaceutically acceptable composition of Paragraph [000170], wherein the $D_{90}$ of said aggregates is less than about 50 μm.

The pharmaceutically acceptable composition of any one of Paragraphs [000169]-[000171], wherein the mesenchymal stem cells exhibit a $D_{90}$ between about 18 μm and about 25 μm.

The pharmaceutically acceptable composition of Paragraph [000172], wherein the mesenchymal stem cells exhibit a $D_{90}$ between about 20 μm and about 25 μm.

A method of preparing a composition of purified mesenchymal stem cells comprising the steps of:
(i) obtaining a cell suspension comprising a plurality of mesenchymal stem cells;
(ii) simultaneously selecting mesenchymal stem cells from the suspension based on mass and diameter.

The method of Paragraph [000174], further comprising the step of contacting said suspension with a wash solution.

The method of Paragraph [000175], wherein said composition comprises one or more mesenchymal stem cell aggregates and the aggregates exhibit a $D_{90}$ of said less than about 150 μm.

The method of Paragraph [000176], the aggregates exhibit a $D_{90}$ of said less than about 100 μm.

The method of Paragraph [000177], the aggregates exhibit a $D_{90}$ of said less than about 50 μm.

The method of Paragraph [000174], wherein said composition comprises no detectable mesenchymal stem cell aggregates.

A pharmaceutically acceptable composition comprising purified mesenchymal stem cells, wherein the mesenchymal stem cells exhibit a $D_{90}$ between about 18 μm and about 30 μm.

The pharmaceutically acceptable composition of Paragraph [000180], wherein the mesenchymal stem cells exhibit a $D_{90}$ between about 18 μm and about 25 μm.

The pharmaceutically acceptable composition of Paragraph [000181], wherein the mesenchymal stem cells exhibit a $D_{90}$ between about 20 μm and about 25 μm.

The composition of any one of Paragraphs [000180]-[000182], further comprising DMSO.

The composition of Paragraph [000183], comprising about 10% DMSO.

The composition of Paragraph [000183], comprising about 3.8% DMSO.

A method of preparing a pharmaceutical mesenchymal stem cell composition comprising the steps of:
(i) Obtaining a mesenchymal stem cell suspension which comprises a plurality of mesenchymal stem cells and mesenchymal stem cell aggregates;
(ii) Contacting the suspension with a wash solution to create a mixed suspension;
(iii) Agitating the mixed suspension with a centrifugal filtration device until the mesenchymal stem cell aggregates exhibit a $D_{90}$ of less than about 150 µm; and,
(iv) Recovering a pharmaceutical mesenchymal stem cell composition.

The method of Paragraph [000186], wherein the mesenchymal stem cell aggregates exhibit the $D_{90}$ of less than about 100 µm.

The method of Paragraph [000187], wherein the mesenchymal stem cell aggregates exhibit the $D_{90}$ of less than about 50 µm.

The method of any one of Paragraphs [000186]-[000188], wherein said pharmaceutical mesenchymal stem cell composition comprises mesenchymal stem cells exhibiting a $D_{90}$ between about 18 µm and about 30 µm.

The method of Paragraph [000189], wherein said pharmaceutical mesenchymal stem cell composition comprises mesenchymal stem cells exhibiting a $D_{90}$ between about 18 µm and about 25 µm.

The method of Paragraph [000190], wherein said pharmaceutical mesenchymal stem cell composition comprises mesenchymal stem cells exhibiting a $D_{90}$ between about 20 µm and about 25 µm.

A composition comprising a population of purified mesenchymal stem cells obtained by the method of any one of Paragraphs [000186]-[000191], wherein viability of the cells is greater than about 70%.

The composition of Paragraph [000192], wherein viability of the cells is greater than about 80%.

The composition of any one of Paragraphs [000186]-[000193], further comprising DMSO.

The composition of Paragraph [000194], comprising about 10% DMSO.

The composition of Paragraph [000194], comprising about 3.8% DMSO.

A pharmaceutically acceptable composition comprising purified mesenchymal stem cells, wherein the composition comprises one or more mesenchymal stem cell aggregates and said aggregates exhibit a $D_{90}$ of less than about 150 µm; and wherein the mesenchymal stem cells exhibit a $D_{90}$ between about 18 µm and about 30 µm.

The pharmaceutically acceptable composition of Paragraph [000197], wherein said aggregates exhibit a $D_{90}$ of less than about 100 µm.

The pharmaceutically acceptable composition of Paragraph [000198], wherein said aggregates exhibit a $D_{90}$ of less than about 50 µm.

The pharmaceutically acceptable composition of any one of Paragraphs [000197]-[000199], wherein the mesenchymal stem cells exhibit a $D_{90}$ between about 18 µm and about 25 µm.

The pharmaceutically acceptable composition of Paragraph [000200], wherein the mesenchymal stem cells exhibit a $D_{90}$ between about 20 µm and about 25 µm.

The pharmaceutically acceptable composition of any one of Paragraphs [000197]-[000201], wherein said composition comprises between about 7 µg/mL and about 15 µg/mL residual bovine serum albumin.

The pharmaceutically acceptable composition of Paragraph [000202], wherein said composition comprises between about 8 µg/mL and about 12 µg/mL residual bovine serum albumin.

A method of selecting a cell suspension containing at least one non-human protein for administration to a patient comprising the steps of:
(a) obtaining at least one sample representative of said cell suspension;
(b) determining a level of said non-human protein present in said sample; and
(c) identifying said cell suspension as suitable for administration to a patient when said sample contains less than about 42 micrograms of said non-human protein per milliliter.

The method of Paragraph [000204], wherein said human cells are mesenchymal stem cells.

The method of Paragraph [000204], wherein said non-human protein is albumin.

The method of Paragraph [000204], wherein said non-human protein is bovine serum albumin.

The method of Paragraph [000206] or [000207], wherein step (b) comprises:
i. contacting said sample with at least one anti-albumin antibody; and
ii. quantifying a level of albumin in said sample.

The method of Paragraph [000204], wherein said non-human protein is trypsin.

The method of Paragraph [000204], wherein said non-human protein is porcine trypsin.

The method of Paragraph [000209] or [000210], wherein step (b) comprises:
i. contacting said sample with at least one agent that selectively binds to trypsin; and
ii. quantifying a level of trypsin in said sample.

The method of Paragraph [000211], wherein said at least one agent is a trypsin inhibitor.

The method of Paragraph [000211], wherein said at least one agent is an anti-trypsin antibody.

The method of Paragraph [000204], wherein step (b) comprises:
i. contacting said sample with an immobilized trypsin inhibitor to form an immobilized trypsin inhibitor-trypsin conjugate;
ii. contacting said immobilized conjugate with an anti-trypsin antibody to form an immobilized trypsin inhibitor-trypsin-antibody complex; and
iii. detecting a signal generated by said complex.

A pharmaceutical composition selected by the method of any one of Paragraphs [000204], [000209]-[000210], or [000212]-[000214].

A method of treating or preventing a disease or disorder in a subject, comprising the steps of:
(a) incubating human cells in media comprising a non-human protein;
(b) selecting a suspension of incubated cells containing less than about 42 micrograms of said non-human protein per milliliter;
(c) administering said suspension of cells to said subject.

The method of Paragraph [000216], wherein said human cells are mesenchymal stem cells.

The method of Paragraph [000216], wherein said non-human protein is albumin.

The method of Paragraph [000216], wherein said non-human protein is bovine serum albumin.

The method of Paragraph [000218] or [000219], wherein step (b) comprises:

i. contacting said sample with at least one anti-albumin antibody; and
ii. quantifying a level of albumin in said sample.

The method of Paragraph [000216], wherein said non-human protein is trypsin.

The method of Paragraph [000216], wherein said non-human protein is porcine trypsin.

The method of Paragraph [000221] or [000222], wherein step (b) comprises:
i. contacting said sample with at least one agent that selectively binds to trypsin; and
ii. quantifying a level of trypsin in said sample.

The method of Paragraph [000223], wherein said at least one agent is a trypsin inhibitor.

The method of Paragraph [000223], wherein said at least one agent is an anti-trypsin antibody.

The method of Paragraph [000216], wherein step (b) comprises:
i. contacting said sample with an immobilized trypsin inhibitor to form an immobilized trypsin inhibitor-trypsin conjugate;
ii. contacting said immobilized conjugate with an anti-trypsin antibody to form an immobilized trypsin inhibitor-trypsin-antibody complex; and
iii. detecting a signal generated by said complex.

A method of manufacturing a cellular therapy product comprising the steps of:
(a) incubating human cells in a solution comprising a non-human protein;
(b) adding a volume of a liquid vehicle to said cells to obtain a pharmaceutically acceptable cell suspension;
(c) obtaining at least one sample representative of said pharmaceutically acceptable cell suspension;
(d) quantifying an amount of said non-human protein present in said sample; and
(e) retaining said cell suspension for administration to a patient when said sample contains less than about 42 micrograms of said non-human protein per milliliter.

The method of Paragraph [000227], further comprising retaining said cell suspension for administration to a patient when said sample contains less than about 30 micrograms of said non-human protein per milliliter.

The method of Paragraph [000227], further comprising retaining said cell suspension for administration to a patient when said sample contains less than about 25 micrograms of said non-human protein per milliliter.

The method of Paragraph [000227], further comprising retaining said cell suspension for administration to a patient when said sample contains less than about 13 micrograms of said non-human protein per milliliter.

The method of Paragraph [000227], further comprising retaining said cell suspension for administration to a patient when said sample contains less than about 10 micrograms of said non-human protein per milliliter.

The method of Paragraph [000227], further comprising retaining said cell suspension for administration to a patient when said sample contains between about 7 and about 15 micrograms of said non-human protein per milliliter.

The method of Paragraph [000227], further comprising retaining said cell suspension for administration to a patient when said sample contains between about 8 and about 12 micrograms of said non-human protein per milliliter.

The method of Paragraph [000227], wherein said human cells are adherent cells.

The method of Paragraph [000227], wherein said human cells are mesenchymal stem cells.

The method of Paragraph [000227], wherein said non-human protein is albumin.

The method of Paragraph [000227], wherein said non-human protein is bovine serum albumin.

The method of Paragraph [000236] or [000237], wherein step (d) comprises:
i. contacting said sample with at least one anti-albumin antibody; and
ii. quantifying a level of albumin in said sample.

The method of Paragraph [000227], wherein said non-human protein is trypsin.

The method of Paragraph [000227], wherein said non-human protein is porcine trypsin.

The method of Paragraph [000239] or [000240], wherein step (d) comprises:
i. contacting said sample with at least one agent that selectively binds to trypsin; and
ii. quantifying a level of trypsin in said sample.

The method of Paragraph [000241], wherein said at least one agent is a trypsin inhibitor.

The method of Paragraph [000241], wherein said at least one agent is an anti-trypsin antibody.

The method of Paragraph [000239] or [000240], wherein step (d) comprises:
i. contacting said sample with an immobilized trypsin inhibitor to form an immobilized trypsin inhibitor-trypsin conjugate;
ii. contacting said immobilized conjugate with an anti-trypsin antibody to form an immobilized trypsin inhibitor-trypsin-antibody complex; and
iii. detecting a signal generated by said complex.

A method of manufacturing a cellular therapy product comprising the steps of:
(a) incubating human cells in a solution comprising a non-human trypsin;
(b) adding a volume of a liquid vehicle to said cells to obtain a pharmaceutically acceptable cell suspension;
(c) obtaining at least two samples representative of said pharmaceutically acceptable cell suspension
(d) determining a trypsin level in a first sample;
(e) incubating a second sample in a solution comprising at least one agent that selectively binds trypsin to obtain a control;
(f) determining a trypsin level in said control;
(g) comparing the trypsin level in said first sample with the trypsin level in said control to obtain a trypsin level in said cell suspension; and
(h) retaining said cell suspension of cells for administration to a patient when said cell suspension contains less than about 30 micrograms of trypsin per milliliter.

The method of Paragraph [000245], further comprising retaining said cell suspension when said cell suspension contains less than about 25 micrograms of trypsin per milliliter.

The method of Paragraph [000245], further comprising retaining said cell suspension when said cell suspension contains less than about 13 micrograms of trypsin per milliliter.

The method of Paragraph [000245], further comprising retaining said cell suspension when said cell suspension contains less than about 10 micrograms of trypsin per milliliter.

The method of Paragraph [000245], further comprising retaining said cell suspension when said cell suspension contains between about 7 and about 15 micrograms of trypsin per milliliter.

The method of Paragraph [000245], further comprising retaining said cell suspension when said cell suspension contains between about 8 and about 12 micrograms of trypsin per milliliter.

The method of Paragraph [000245], wherein said human cells are mesenchymal stem cells.

The method of Paragraph [000245], wherein said agent is a trypsin inhibitor.

The method of Paragraph [000245], wherein said agent is an anti-trypsin antibody.

A cellular therapy product manufactured by the method of any one of Paragraphs [0002227]-[000237], [000239]-[000240], or [000245]-[000253].

A cellular therapy product manufactured by the method of Paragraph [000238].

A cellular therapy product manufactured by the method of Paragraph [000241].

A cellular therapy product manufactured by the method of Paragraph [000242].

A cellular therapy product manufactured by the method of Paragraph [000243].

A cellular therapy product manufactured by the method of Paragraph [000244].

A pharmaceutically acceptable cell suspension comprising human mesenchymal stem cells and at least one non-human protein, wherein said cell suspension contains less than about 42 micrograms of said non-human protein per milliliter.

The cell suspension of Paragraph [000260], further comprising retaining said cell suspension for administration to a patient when said sample contains less than about 30 micrograms of said non-human protein per milliliter.

The cell suspension of Paragraph [000260], further comprising retaining said cell suspension for administration to a patient when said sample contains less than about 25 micrograms of said non-human protein per milliliter.

The cell suspension of Paragraph [000260], further comprising retaining said cell suspension for administration to a patient when said sample contains less than about 13 micrograms of said non-human protein per milliliter.

The cell suspension of Paragraph [000260], further comprising retaining said cell suspension for administration to a patient when said sample contains less than about 10 micrograms of said non-human protein per milliliter.

The cell suspension of Paragraph [000260], further comprising retaining said cell suspension for administration to a patient when said sample contains between about 7 and about 15 micrograms of said non-human protein per milliliter.

The cell suspension of Paragraph [000260], further comprising retaining said cell suspension for administration to a patient when said sample contains between about 8 and about 12 micrograms of said non-human protein per milliliter.

The cell suspension of Paragraph [000260], wherein said non-human protein is albumin.

The cell suspension of Paragraph [000260], wherein said non-human protein is bovine serum albumin.

The cell suspension of Paragraph [000260], wherein said non-human protein is trypsin.

The cell suspension of Paragraph [000260], wherein said non-human protein is porcine trypsin.

What is claimed is:

1. A pharmaceutically acceptable composition comprising purified mesenchymal stem cells, wherein the composition comprises one or more mesenchymal stem cell aggregates and wherein the diameter which is greater than 90% or more of said aggregates ($D_{90}$) is less than about 150 μm.

2. The pharmaceutically acceptable composition of claim 1, wherein the $D_{90}$ of said aggregates is less than about 100 μm.

3. The pharmaceutically acceptable composition of claim 2, wherein the $D_{90}$ of said aggregates is less than about 50 μm.

4. The pharmaceutically acceptable composition of claim 1, wherein the portion of the purified mesenchymal stem cells which are viable is greater than about 70%.

5. The pharmaceutically acceptable composition of claim 4, wherein the portion of the purified mesenchymal stem cells which are viable is greater than about 80%.

6. A pharmaceutically acceptable composition comprising purified mesenchymal stem cells, wherein the composition comprises less than about 55 μg/mL bovine serum albumin and wherein the composition comprises one or more mesenchymal stem cell aggregates and wherein the diameter which is greater than 90% of said aggregates ($D_{90}$) is between about 18 μm and about 30 μm.

7. The composition of claim 6, wherein the composition comprises less than about 42 μg/mL bovine serum albumin.

8. The composition of claim 7, wherein the composition comprises less than about 25 μg/mL bovine serum albumin.

9. The composition of claim 8, wherein the composition comprises less than about 13 μg/mL bovine serum albumin.

10. The composition of claim 9, wherein the composition comprises less than about 10 μg/mL bovine serum albumin.

11. The composition of claim 6, wherein the composition comprises between about 7 μg/mL and about 15 μg/mL bovine serum albumin.

12. The composition of claim 11, wherein the composition comprises between about 8 μg/mL and about 12 μg/mL bovine serum albumin.

13. The composition of claim 6, wherein the $D_{90}$ is between about 18 μm and about 25 μm.

14. The composition of claim 6, wherein the portion of the purified mesenchymal stem cells which are viable is greater than about 70%.

15. The composition of claim 14, wherein the portion of the purified mesenchymal stem cells which are viable is greater than about 80%.

* * * * *